United States Patent
Rojas

(10) Patent No.: US 10,656,158 B2
(45) Date of Patent: May 19, 2020

(54) IDENTIFICATION OF ENZYME ACTIVITY THROUGH DETERMINATION OF ITS LOCALIZATION

(71) Applicant: International Business Machines Corporation, Armonk, NY (US)

(72) Inventor: Pablo Meyer Rojas, Brooklyn, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 68 days.

(21) Appl. No.: 15/909,174

(22) Filed: Mar. 1, 2018

(65) Prior Publication Data

US 2018/0188261 A1 Jul. 5, 2018

Related U.S. Application Data

(63) Continuation-in-part of application No. 14/583,841, filed on Dec. 29, 2014, now abandoned.

(60) Provisional application No. 61/944,200, filed on Feb. 25, 2014.

(51) Int. Cl.
| | |
|---|---|
| *C12Q 1/25* | (2006.01) |
| *G01N 33/58* | (2006.01) |
| *G01N 21/64* | (2006.01) |
| *G01N 33/52* | (2006.01) |
| *G01N 33/573* | (2006.01) |
| *G01N 33/50* | (2006.01) |
| *A61K 45/00* | (2006.01) |

(52) U.S. Cl.
CPC .......... *G01N 33/582* (2013.01); *A61K 45/00* (2013.01); *C12Q 1/25* (2013.01); *G01N 21/6486* (2013.01); *G01N 33/5035* (2013.01); *G01N 33/52* (2013.01); *G01N 33/573* (2013.01); *G01N 21/6458* (2013.01)

(58) Field of Classification Search
CPC .... C12Q 1/25; G01N 33/5035; G01N 33/582; G01N 33/58

See application file for complete search history.

(56) References Cited

U.S. PATENT DOCUMENTS

2015/0241411 A1 8/2015 Meyer Rojas

OTHER PUBLICATIONS

An et al. 2008; Reversible compartmentalization of de novo purine biosynthetic complex in living cells. Science. 320: 103-106.*
Pinho et al. 2005; Recruitment of penicillin-binding protein PBP2 to the division site of *Staphylococcus aureus* is dependent on transpeptidation substrates. Molecular Microbiology. 55(3): 799-807.*
Scheffers et al. 2005; Bacterial cell wall synthesis: New insights from localization studies. Microbiology and Molecular Biology Reviews. 69(4): 585-607.*
Schoberer et al. 2013; Time-resolved fluorescence imaging reveals differential interactions of N-glycan processing enzymes across the Golgi stack in planta. Plant Physiology. 161: 1737-1754.*
List of IBM Patents or Patent Applications Treated as Related; (Appendix P), Filed Mar. 1, 2018; 2 pages.
U.S. Appl. No. 15/909,174, filed Mar. 1, 2018.
U.S. Appl. No. 14/583,841, filed Dec. 29, 2014, 2015-0241411.

* cited by examiner

*Primary Examiner* — Karen Cochrane Carlson
(74) *Attorney, Agent, or Firm* — Cantor Colburn LLP; Vazken Alexanian

(57) ABSTRACT

A method of determining enzyme activity and identifying and classifying cellular targets, enzymatic pathways, and enzymatic agents involved in regulating metabolism in order to treat pathophysiological disorders. Monitoring enzyme activity is performed via a label-free bio cellular assay or fluorescence imaging. The identified and classified agents are used, together with a therapeutic agent, in the treatment of various metabolism-related diseases.

11 Claims, 3 Drawing Sheets

IDENTIFICATION OF ENZYME ACTIVITY THROUGH DETERMINATION OF ITS LOCALIZATION

PRIORITY

This application is a continuation-in-part of and claims priority from U.S. patent application Ser. No. 14/583,841, filed on Dec. 29, 2014, entitled "IDENTIFICATION OF ENZYME ACTIVITY THROUGH DETERMINATION OF ITS LOCALIZATION," which is a non-provisional of and claims priority from U.S. Patent Application Ser. No. 61/944,200, filed on Feb. 25, 2014, entitled "IDENTIFICATION OF ENZYME ACTIVITY THROUGH DETERMINATION OF ITS LOCALIZATION," the entire contents of both applications are incorporated herein by reference.

BACKGROUND

The present invention generally relates to methods of determining enzyme activity involved in regulating metabolism. More particularly, the present invention relates to identifying cellular targets, enzymatic pathways, and enzymatic agents in order to treat pathophysiological disorders.

Enzymes are responsible for the metabolic needs, capabilities, and possibilities of living organisms. Enzymes are required in almost all chemical reactions in a cell and their activity determines which metabolic pathways can occur. While enzymes play a very important role in sustaining life, the malfunction of a single enzyme, through a mutation, deletion, etc., can lead to diseases, such as cancer or diabetes. Therefore, it is important to determine which enzymes are active in different disease situations.

Enzyme activity can be measured using either direct or indirect methods. Indirect methods include measuring the synthesis rate of its product or the consumption rate of its substrate as measured by mass spectroscopy, liquid chromatography, or via in vitro chemical assays. Direct methods include magnetic resonance imaging to measure in vivo enzyme activity. However, these methods are cumbersome and cannot be scaled to many enzymes or to different time points.

Accordingly, improved methods for determining enzyme activity are needed, in particular how enzyme localization reflects enzyme activity.

SUMMARY

One aspect of the present invention provides a method of identifying cellular targets involved in regulating enzyme condensation dynamics which includes the steps of providing a cell that has a cellular target, contacting the cell with a molecule that interacts with the cellular target forming a molecule-contacted cell, exposing the molecule-contacted cell to an enzyme condensation promoting agent, exposing the molecule-contacted cell to an enzyme condensation disrupting agent, monitoring the state of enzyme condensation of the molecule-contacted cell during or after exposure to the enzyme condensation promoting agent and the enzyme condensation disrupting agent, and determining the molecule's ability to regulate the state of enzyme condensation.

Another aspect of the present invention provides a method of identifying an enzyme condensation dynamics modulating pathway which includes the steps of providing a cell that has a cellular target, contacting the cell and (i) a cellular pathway modulator that interacts with the cellular target and (ii) a cellular target specific ligand forming a cellular pathway modulator and ligand-contacted cell, exposing the cellular pathway modulator and ligand-contacted cell to an enzyme condensation modulating agent, assaying the cell response to the enzyme condensation modulating agent, and determining the cellular pathway modulator's ability to regulate the state of enzyme condensation.

Yet another aspect of the present invention provides a method of identifying agents that regulate enzyme condensation dynamics including the steps of providing a cell, forming a molecule-contacted cell by contacting the cell with a molecule, exposing the molecule-contacted cell with an enzyme condensation promoting agent, exposing the molecule-contacted cell with an enzyme condensation disrupting agent, monitoring the state of enzyme condensation of the molecule-contacted cell during or after exposure to the enzyme condensation promoting agent and the enzyme condensation disrupting agent, and determining the modulating ability of the molecule on the state of enzyme condensation.

A further aspect of the present invention provides a method of determining the metabolic state of an enzyme through enzyme condensation comprising the steps of providing a cell having a cellular target, attaching a reporter protein to the cellular target by contacting the reporter protein with the cell, exposing the cell with an enzyme condensation promoting agent, exposing the cell with an enzyme condensation disrupting agent, monitoring the state of enzyme condensation of the cell during or after exposure to the enzyme condensation promoting agent and the enzyme condensation disrupting agent, and determining the state of enzyme condensation.

Yet another aspect of the present invention provides a method of treating a subject having a disease that is pathophysiologically related to enzyme localization, the method including the step of administering a therapeutically effective amount of an enzyme localization dynamics modulator for modulating enzyme condensation.

According to other aspects of the present invention, a method of analyzing enzyme activity within a cell includes attaching a fluorescent reporter to an enzyme within the cell to form a tagged enzyme. The enzyme is a part of a metabolic pathway. The method includes contacting the cell with a molecule that directly or indirectly affects localization of the tagged enzyme. The method further includes assaying the tagged enzyme within the cell to determine whether the tagged enzyme is localized or diffuse within the cell. The method also includes determining, based on assaying the tagged enzyme within the cell, whether the molecule promotes or disrupts localization of the tagged enzyme. The method includes determining whether the tagged enzyme is metabolically active or inactive, based on whether the tagged enzyme is localized or diffuse, respectively.

According to one or more aspects of the invention, a method of determining a metabolic state of an enzyme using enzyme localization includes attaching a fluorescent reporter to an enzyme within the cell to form a tagged enzyme. The enzyme is a part of a metabolic pathway. The method includes contacting the cell with a molecule that directly or indirectly affects localization of the tagged enzyme. The method includes assaying, by fluorescence imaging, the tagged enzyme within the cell to determine whether the tagged enzyme is localized or diffuse within the cell. The method also includes determining, based on assaying the tagged enzyme within the cell, whether the molecule promotes or disrupts localization of the tagged enzyme. The method includes determining whether the tagged enzyme is metabolically active or inactive, based on whether the tagged enzyme is localized or diffuse, respectively. The method further includes determining whether the metabolic pathway in the cell is active or inactive, based on whether the enzyme is active or inactive, respectively.

The present invention has many advantages over other methods, such as mass spectroscopy, liquid chromatography, magnetic resonance imaging, etc. The present method can be scaled to many enzymes at a lower cost and it is also more flexible and simpler to implement.

BRIEF DESCRIPTION OF THE DRAWINGS

These and further features of the present invention will be apparent with reference to the following description and drawing, wherein.

DETAILED DESCRIPTION OF THE PREFERRED EMBODIMENT

Figure 1:
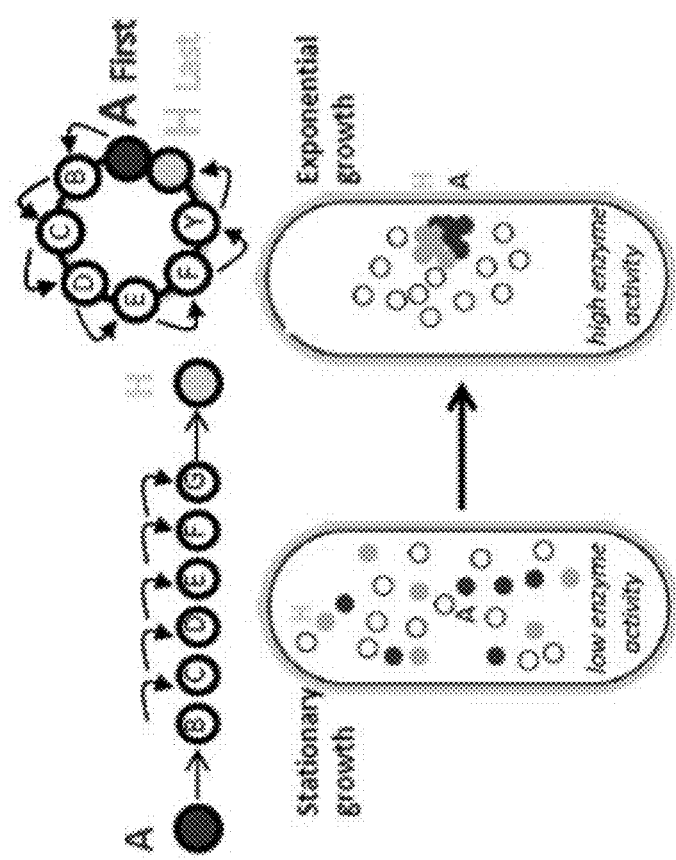
FIG. 1 is a schematic diagram illustrating the organization of enzymes, A to H, in a metabolic pathway, going from diffuse localization in the cytoplasm when the enzymes are not active (left) to a discrete concentration of enzymes when the pathway is active (right)

The following detailed description of various preferred embodiments will illustrate the general principles of the present invention with reference to methods of identifying cellular targets involved in enzyme condensation dynamics, enzyme condensation dynamics pathways, and enzyme condensation dynamics modulators, and their use in the treatment of pathophysiological diseases for purposes of clarity and not by way of limitation. The application of the preferred embodiments in other contexts will be apparent to those skilled in the art given the benefit of this disclosure.

Although the enzymatic cascades that underlie cellular biosynthesis are understood, comparatively little is known about the rules that determine their cellular organization. The image of a cell as a "bag of enzymes" has given way to a view where molecules and proteins localize at the right time in the right place in order to perform their necessary functions. However, enzymes involved in the most basic metabolic functions are generally thought to be freely diffusing in the cytoplasm. The existence of large multi-enzyme complexes, as opposed to freely diffusing enzymes, could either be determined by constraints limited to highly specialized reactions or a general mechanism used throughout the cell to achieve a generic metabolic function.

Globular non-membrane bound enzymes of bacterial and eukaryotic cells concentrate to cytoplasmic foci when active and are diffuse when they are inactive. When a metabolic pathway is active, the first and last enzymes of such biosynthetic pathway condense to precise cytoplasmic foci, but are homogenously distributed during stationary growth, suggesting that the concentration of enzymes to discrete foci occurs when they are most active. Thus, enzyme condensation reflects the activity state of a cell's metabolism, following a pathway specific first-or-last enzyme localization rule and also interconnecting active metabolic pathways. Such an enzyme condensation event is hereby described as a direct way to screen for agents regulating cell metabolism via the regulation of the dynamics of enzyme condensates.

The invention includes determining the metabolic state, i.e., active or inactive, of each kind of enzyme in the organism under study. This is done by determining whether the enzyme is focalized (active) or diffuse (inactive) in the cytoplasm. One way of determining the metabolic state of an enzyme is to attach a fluorescent reporter protein or any other sort of reporter to the carboxyl terminal portion or any other portion of each enzyme and use a method, such as a fluorescent microscope, to determine whether the enzyme is focalized (condensed) or diffuse in the cell cytoplasm.

Reporters of different wavelengths can be attached to different enzymes, allowing one to determine the enzymatic activity of multiple enzymes simultaneously. In other circumstances, enzyme activity can be determined one enzyme at a time.

This method of identifying enzyme activity has many advantages over other methods, such as mass spectroscopy, liquid chromatography, magnetic resonance imaging, etc. The present method can be scaled to many enzymes at a lower cost. It is also more flexible and simpler to implement.

Figure 2:
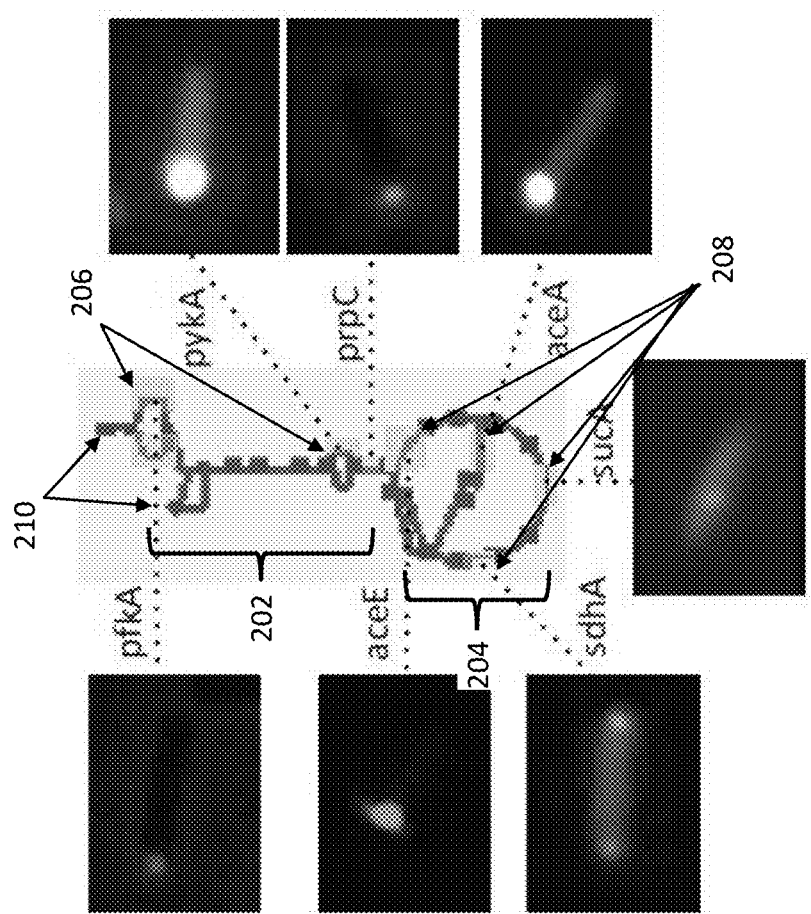
FIG. 2 is a diagram of images of enzymes during glycolysis and the TCA cycle, showing both localized enzyme activity (active) and diffuse enzyme activity (not active)

FIGS. 1 and 2 illustrates embodiments of the invention. FIG. 1 shows the condensation of enzymes. During low enzyme activity on the left side of the figure, the enzymes are diffuse throughout the cell. During high enzyme activity on the right side of the figure, the enzymes localize to particular foci within the cellular cytoplasm. Enzymes A through H are part of a biosynthetic pathway within the cell that form a cellular product. During stationary growth, enzyme activity and metabolic activity is low and each of the enzymes A through H are diffusely distributed throughout the cell (left side of FIG. 1). However, during exponential rapid growth, enzyme activity and metabolic activity are high and at least the first and last enzymes A and H, respectively, are concentrated or localized to discrete areas within the cellular cytoplasm (right side of FIG. 1). Thus, cellular growth and metabolism can directly correlate with enzyme activity, as well as metabolic activity of the pathway and cell itself.

FIG. 1 thus illustrates embodiments of the invention. According to one or more embodiments, a method includes providing a cell that includes an enzyme of interest. The enzyme of interest is a part of a biosynthetic pathway of interest within the cell. The enzyme is tagged with a fluorescent reporter (protein or molecule) according to some embodiments. The enzyme is a globular non-membrane bound enzyme according to some embodiments. To assay and analyze the enzyme activity within the cell, the cell is then contacted with a molecule that may promote or disrupt localization of the tagged enzyme within the cell (or promote activity within the cell as shown on the right side of FIG. 1). The state of enzyme condensation is monitored. The method includes determining the molecule's ability to modulate the state of enzyme condensation (or localization). Such determination includes observing whether the tagged enzyme becomes localized or diffuse within the cell during or after exposure to the molecule. The step of monitoring the state of enzyme condensation during or after being exposed to the molecule can be done through the use of fluorescence imaging of an enzyme.

Although the enzyme is tagged with a fluorescent reporter that can be assayed and imaged by microscopy, embodiments of the invention include a method that includes using a label-free biosensor-based cellular assay to assess enzyme activity.

FIG. 2 shows images of active (localized) and inactive (diffuse) enzymes from glycolysis 202 and the TCA cycle 204 in an *E. coli* bacterial cell, which illustrates embodiments of the invention. The central rectangle in FIG. 2 illustrates enzymes in glycolysis 202 and the TCA cycle 204. Each dark box on the pathway (for example see arrows at 210) represents an enzyme in the pathway. To assess enzyme activity, each enzyme is tagged with a fluorescent reporter. Then during exponential growth of the cells, enzyme activity of each of the enzymes is assessed and assayed individually. The highlighted and expanded boxes 206 and 208 illustrate enzymes that are localized during active glycolysis 202 and the TCA cycle 204, respectively. The enzymes appear to be localized and therefore active based on the bright fluorescent spots. The remaining enzymes in the pathways are diffuse during glycolysis 202 and the TCA cycle 204. Thus, as shown enzyme activity of individual enzymes can be analyzed based on whether they are localized or diffuse within the cell. To promote or disrupt enzyme localization, modulating molecules (which can be enzyme condensation promoting agents or enzyme condensation disrupting agents) can be added to the cells before or during the assay.

FIG. 2 thus illustrates a method according to embodiments of the invention. The method includes providing a cell that includes a cellular target, which can be a tagged enzyme of interest within a biosynthetic or biochemical pathway of interest. To assess enzyme activity, the cell is then exposed to a molecule that can interact with the enzyme of interest. The molecule can be, for example, an enzyme condensation promoting agent or an enzyme condensation disrupting agent. During or after exposure to the promoting and/or disrupting agents, the state of enzyme condensation is then monitored to determine the modulating ability of the molecule on the state of enzyme condensation. As in FIG. 1, the step of monitoring the state of enzyme condensation during or after being exposed to enzyme condensation promoting and/or disrupting agents can be done through the use of fluorescence imaging of an enzyme that is part of the enzyme condensation complex. In other embodiments, enzyme activity can be assessed through the use of a label-free biosensor-based cellular assay.

According to one or more embodiments, the cell is a HeLa cell. According to other embodiments, the cell is a bacterial cell. According to one or more embodiments, the cell is a eukaryotic cell.

The molecule that is used to promote or disrupt condensation (localization) of the enzyme is any type of molecule that can affect enzyme activity and thereby disrupt or promote enzyme localization. The molecule can be selected, for example, based on a known or possible interaction with or effect on the enzyme of interest or the pathway in which the enzyme is involved with. The molecule interacts either directly with the enzyme itself to promote or disrupt activity, or indirectly affects the enzyme. For example, the molecule, such as a hormone, can have an indirect effect on the enzyme by altering the concentration of the enzyme. Other possible indirect effects include altering the concentration of an enzyme catalyst or ligand, for example. The molecule that interacts with the cellular target (the tagged enzyme) includes, but is not limited to, hormones, signaling effectors, antibodies, antibiotics (such as ampicillin, vancomycin, fosfomycin, erythromycin), bacterial products (such as rapamycin, tryptone, stauromycin, leptomycin-B), plant derived products, synthetic chemicals (e.g., IPTG) or chemical products (e.g., NACL, d-glucose, $CaCl_2$, $MgCl_2$, $CuCl_2$, $ZnCl_2$, $MnSO_4$, $MgCl_2$, $(NH_4)_2SO_4$, $Na_2MoO_4$, $CoCl_2$, and $Ca(NO_3)_2$), amino acids (such as l-glutamic acid, l-leucine, l-valine, l-threonine, l-methionine, l-histidine) and carbohydrates and carboxylic acids, or any combination thereof. Any one or more of the foregoing molecules can also be added to the cell and enzyme to initiate activity of the enzyme and/or biochemical pathway prior to adding a molecule to promote localization or disrupt localization.

The enzyme condensation (or localization) promoting agent, as mentioned above, can affect enzyme activity either directly or indirectly. The enzyme condensation promoting agent can directly or indirectly promote enzyme activity, resulting in enzyme localization. The enzyme condensation promoting agent also can directly or indirectly affect enzyme activity by inhibiting enzyme decondensation, which could also result in the enzyme being maintained in a condensed state. The enzyme condensation promoting agent can be, but is not limited to, an antibiotic (e.g., fosfomycin or vancomycin), a hormone (e.g., insulin), a signaling effector (e.g., EGF), a chemical product (e.g., glucose), and an amino acid (e.g., l-methionine), or a combination thereof. The specific activity of the enzyme condensation promoting agent depends on the type of cell and the particular enzyme.

When an enzyme condensation promoting agent is used in combination with an enzyme condensation disrupting agent, the agents can be used sequentially. However, enzyme activity is assayed in between or during exposure to the promoting agent and the disrupting agent. In some circumstances, the enzyme condensation promoting agent can contact the cell before the enzyme condensation disrupting agent, while in others, the enzyme condensation disrupting agent contacts the cell before the enzyme condensation promoting agent. In either case, the time between contact of the promoting agent and the disrupting agent can be, but is not limited to, 1, 5, 10, 15, 30, or 60 minutes. The time between cell contacts of the agents can be, but is not limited to 1, 2, 3, 4, 5, 10, 12, 18, or 24 hours.

The enzyme condensation (localization) disrupting agent, as mentioned above, can affect enzyme activity either directly or indirectly. The enzyme condensation disrupting agent can directly or indirectly inhibit enzyme activity, resulting in enzyme de-localization or diffusion. The enzyme condensation disrupting agent can be, but is not limited to, an antibody (e.g., anti-her2), an antibiotic (e.g., fosfomycin or vancomycin), and a bacterial product (e.g., rapamycin), or any combination thereof. The specific activity of the enzyme condensation disrupting agent depends on the type of cell and the particular enzyme.

The molecule's ability to affect the dynamics of the state of enzyme condensation, i.e., localized or diffuse, demonstrates that the cellular target of the molecule (either affecting the enzyme directly or indirectly) plays a role in regulating enzyme condensation dynamics. The molecule can be, but is not limited to, an agonist of the enzyme.

Another way to identify enzyme activity is via enzyme condensation dynamics modulating pathways. For example, this can be accomplished by forming a cellular pathway modulator and ligand-contacted cell. A cell with a known enzyme of interest is (i) contacted with a cellular pathway modulator that interacts with the enzyme of interest and (ii) contacted with a ligand specific for the enzyme. The contacted cell is then exposed to an enzyme condensation modulating agent and the response is then assayed. This allows one to determine the regulatory ability of the cellular pathway modulator on the state of enzyme condensation.

The ability of the cellular pathway modulator to regulate enzyme condensation dynamics indicates that the pathway is an enzyme condensation dynamics modulating pathway.

The enzyme specific ligand is typically an agonist. The ligand can be a ligand specific for the enzyme, or can be a molecule that mimics the ligand and activates the enzyme pathway.

The enzyme modulator may be interference RNA or a kinase inhibitor and can affect different stages of the pathway. For example, some modulators may affect the earlier stages of a pathway, while others may affect the later stages. If a pathway splits into multiple pathways in the later stages, it can be useful to use cellular pathway modulators specific to each pathway.

In some instances, a control is used to compare the effects of the cellular pathway modulator on regulating enzyme condensation dynamics. For example, a cell contacted with a cellular pathway modulator, a ligand, and an enzyme condensation modulating agent may be compared to a control cell that has been contacted with a ligand and enzyme condensation modulating agent.

In some circumstances, the enzyme condensation promoting agent can contact the cell before the enzyme condensation disrupting agent, while in others, the enzyme condensation disrupting agent contacts the cell before the enzyme condensation promoting agent. In either case, the time between contact of the promoting agent and the disrupting agent can be in the range from about 1 to about 60 minutes, and ranges there between. The time between cell contacts of the agents can be from about 1 to about 24 hours, and ranges there between.

Another aspect of this invention provides a method for classifying cellular targets, modulating pathways, and regulating agents based on their regulation of enzyme condensation dynamics. Classification can be based on correlation analysis, wherein the correlation between the enzyme condensation disrupting agent response and the enzyme condensation promoting agent response are determined. Classification can also be based on a similarity analysis, wherein the Hierarchy Euclidean clustering of the enzyme condensation disrupting agent's response and the enzyme condensation promoting agent's response are compared. Correlation or similarity analysis further includes examining the fluorescent patter of a fluorescent enzyme that is part of the enzyme condensation complex, wherein the fluorescent enzyme is introduced inside the cell through gene transfection and expression or through protein delivery.

By identifying and classifying which enzymes are active in different metabolic processes, it is possible to determine which enzymes are active in disease situations. Thus, another embodiment of the present invention provides for the treatment of a disease that is pathophysiologically related to enzyme condensation, such as a metabolic disorder, cancer, or an inflammatory disease. The method includes administering a therapeutically effective amount of an enzyme condensation dynamics modulator (a localization promoter or disrupter for example), which can be an enzyme condensation promoting agent or enzyme condensation disrupting agent. A therapeutically effective amount can range from 1-100 micromol/kg of an enzyme condensation dynamics modulator. The enzyme condensation dynamics modulator or therapeutic agent can be administered in the range from about 1 to 60 minutes apart, and ranges there between or from about 2 to about 72 hours, and ranges there between.

EXAMPLES

The invention is further illustrated by the following examples. The example is provided for illustrative purposes only, and is not to be construed as limiting the scope or content of the invention in any way.

Enzymatic activity of the MurA enzyme in *Bacillus subtilis* was measured in the presence of enzyme condensation modulating agents. MurA enzyme is involved in an enzymatic biosynthetic pathway that catalyzes a biosynthetic precursor of peptidoglycan, a polymer of the cell wall. The agents that were assessed for effects on MurA were antibiotics fosfomycin and vancomycin.

The *B. subtilis* cells were cultivated to express a MurA-CFP conjugate protein (MurA-cyan fluorescent protein) under its natural promoter. After one hour in exponential growth, 1 ml of cell culture was centrifuged. The supernatant was collected and added to 2 ml of melted 3.5% agarose solution in LB. The resulting 1.2% solution of molten agar/culture supernatant was supplemented with 0.5 µg ml$^{-1}$ FM 4-64 dye (N-(3-triethylammoniumpropyl)-4-(6-(4-(diethylamino) phenyl) hexatrienyl) pyridinium dibromide). Then 5 mM fosfomycin or 0.5 µg ml$^{-1}$ vancomycin was added to the well of a culture slide (wells 18 mm diameter× 1.75 mm depth) and covered with a glass slide.

After cooling, the cover glass was removed and two air pockets were cut out of the agarose with a 15 ml tube, leaving a 3-5 mm agar bridge in the center of the well. Seven microliters of the remaining culture was spread over the agar, partially dried and sealed with cover glass. After cooling, the slide was removed and two air pockets were cut out of the agar leaving a 3-5 mm agar bridge in the center of the well. Cells were suspended in LB with FM4-64 dye (0.5 µg ml$^{-1}$) and were added at the agar bridge and covered by a glass coverslip. To prevent drying during the experiment, 50% glycerol was applied to the region of contact between the slide and the coverslip.

The slide was equilibrated in an environmentally controlled chamber at 30° C. (Precision Control Weather Station) for at least 10 min prior to visualization. Images were acquired every 5 minutes for 4 hours, using an Applied Precision Spectris microscope, with a 100× objective using phase contrast and captured by a Hamamatsu Orca-ER camera using Nikon Elements BR software. CFP and TRITC (FM4-64) exposures were 400 ms. Fosfomycin and vancomycin were obtained from Sigma, cerulenin was obtained from Cayman Chemical, and FM4-64 to stain the cellular membranes was from Invitrogen. After 2 hours of imaging, MurA-CFP expressing cells stopped growing, but the condensation of the enzyme could be detected by a bright fluorescent spot.

Figure 3B:
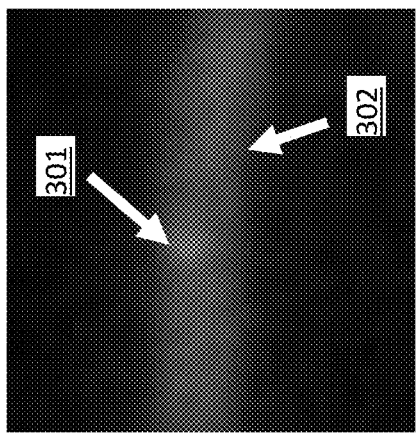
FIG. 3B depicts an image of a fluorescently tagged enzyme in a fast growing cell.
Figure 3A:
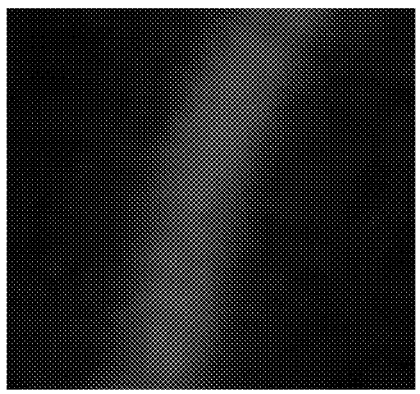
FIG. 3A depicts an image of a fluorescently tagged enzyme in a slow growing cell.

FIGS. 3A-3D show images of the cells. FIG. 3A depicts an image of the slowly growing cells. In the slowly growing cells, or during stationary growth, the MurA-CFP enzyme was diffuse in the cell, without evidence of the MurA-CFP enzyme being focused/localized to any particular area, which suggested that during this slow growth the biosynthetic pathway which MurA is involved in is not active.

FIG. 3B depicts an image of the cells during exponential growth when cellular metabolism is fast. The localized enzyme is shown at region 301, with the diffuse enzyme at region 302. When the cellular metabolism is fast during exponential growth, the MurA-CFP enzyme localized to specific areas in the cell. Thus, during fast growth and metabolism, the MurA biosynthetic pathway was active.

Figure 3D:
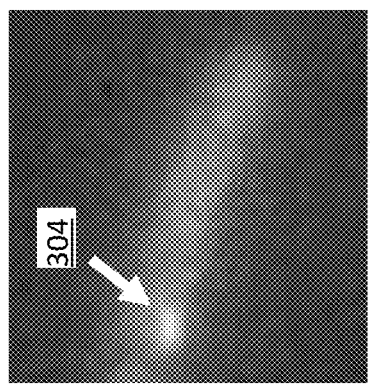
FIG. 3D depicts an image of a fluorescently tagged enzyme that is localized.
Figure 3C:
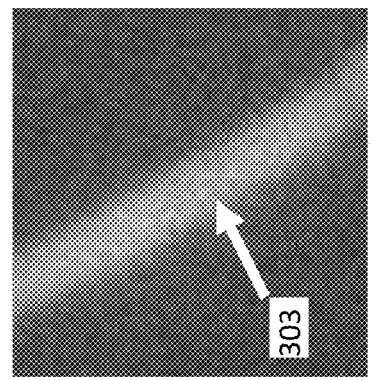
FIG. 3C depicts an image of a fluorescently tagged enzyme that is diffuse.

FIG. 3C depicts an image of the diffuse MurA-CFP after exposure to vancomycin during exponential growth. As shown, the MurA-CFP enzyme was diffuse at region 303. Vancomycin thus appeared to interact with MurA-CFP in a direct or indirect way, such that the enzyme itself was diffuse and the MurA biosynthetic pathway was not active.

FIG. 3D depicts an image of the localized MurA-CFP after exposure to fosfomycin during exponential growth. As shown, the MurA-CFP enzyme was localized at region 304. Fosfomycin thus appeared to interact with MurA-CFP in a direct or indirect way, such that the enzyme itself was localized and the MurA biosynthetic pathway was active. As fosfomycin is a known inhibitor of the MurA enzyme, it was determined that fosfomycin prevented MurA from delocalizing (or decondensing). When fosfomycin was added to the cells during stationary growth before MurA began to localize (not shown), areas of localized MurA-CFP was not observed.

Thus, from the foregoing disclosure and detailed description of certain preferred embodiments for methods for identifying enzyme activity through determination of its localization, and their uses for treating pathophysiological disorders, it is apparent that various modifications, additions, and other alternative embodiments are possible without departing from the scope of the present invention. The embodiments described herein were chosen to provide the best illustration of the present invention, and thus one skilled in the art can practice the invention in ways other than the described embodiments. The present invention is only limited by the claims which follow.

What is claimed is:

1. A method for analyzing enzyme activity within a cell, the method comprising:
    attaching a fluorescent reporter to an enzyme within the cell to form a tagged enzyme, the enzyme being a part of a metabolic pathway;
    contacting the cell with a molecule that affects localization of the tagged enzyme within the cell, wherein the molecule is selected from the group consisting of fosfomycin, insulin, EGF, glucose, and 1-methionine and combinations thereof;
    assaying by fluorescence imaging the tagged enzyme within the cell to determine whether the tagged enzyme is localized or diffuse within the cell;
    wherein, based on whether the tagged enzyme is localized or diffuse within the cell, determining whether the molecule promotes or disrupts localization of the tagged enzyme, respectively; and
    wherein, based on whether the tagged enzyme is localized or diffuse within the cell, determining whether the tagged enzyme is metabolically active or inactive, respectively.

2. The method of claim 1, wherein the active tagged enzyme appears as a bright fluorescent spot during or after assaying.

3. The method of claim 1, wherein the inactive tagged enzyme appears diffuse and without bright fluorescent spots during or after assaying.

4. A method of determining a metabolic state of a metabolic pathway using enzyme localization of two or more enzymes in the metabolic pathway, the method comprising:
    attaching a first fluorescent reporter of a first wavelength to a first enzyme within the cell to form a first tagged enzyme, the first enzyme being a part of a metabolic pathway;
    attaching a second fluorescent reporter of a second wavelength to a second different enzyme within the cell to form a second tagged enzyme, wherein the second enzyme being part of the same metabolic pathways as the first enzyme,
    optionally, attaching fluorescent reporters to additional enzymes within the cell, the additional enzymes being part of the metabolic pathway of the first and second enzymes, wherein the fluorescent reporters having different wavelengths from the other fluorescent reporters attached to other enzymes being part of the metabolic pathway;
    contacting the cell with a molecule that affects localization of the tagged enzymes within the cell;
    assaying, by fluorescence imaging, the tagged enzymes within the cell to determine, simultaneously, whether the tagged enzymes are localized or diffuse within the cell;
    wherein, based on whether the tagged enzymes are localized or diffuse within the cell, determining whether the molecule promotes or disrupts localization of the tagged enzymes, respectively;
    wherein, based on whether the tagged enzymes are localized or diffuse within the cell, determining whether the tagged enzymes are metabolically active or inactive, respectively;
    wherein, based on whether the first enzyme and the second enzyme is active or inactive, determining whether the metabolic pathway in the cell is active or inactive, respectively.

5. The method of claim 4, wherein the molecule is a signaling effector, a hormone, an antibody, an antibiotic, an amino acid, a carbohydrate, a carboxylic acid, or any combination thereof.

6. The method of claim 4, wherein the molecule is an enzyme localization promoting agent that promotes localization of the tagged enzymes within the cell.

7. The method of claim 6, wherein the tagged enzymes appear as a bright fluorescent spot during or after assaying.

8. The method of claim 6, wherein the enzyme localization promoting agent is an antibiotic, a hormone, a signaling effector, a chemical compound, an amino acid, or any combination thereof.

9. The method of claim 4, wherein the molecule is an enzyme localization disrupting agent that disrupts localization of the tagged enzymes within the cell.

10. The method of claim 9, wherein the tagged enzymes appear diffuse and without bright fluorescent spots during or after assaying.

11. The method of claim 9, wherein the enzyme localization disrupting agent is an antibody, an antibiotic, a bacterial product, or any combination thereof.

* * * * *